United States Patent
Garbey et al.

(10) Patent No.: US 10,499,831 B2
(45) Date of Patent: Dec. 10, 2019

(54) SYSTEMS AND METHODS FOR MEDICAL PROCEDURE MONITORING

(71) Applicants: UNIVERSITY OF HOUSTON, Houston, TX (US); THE METHODIST HOSPITAL, Houston, TX (US)

(72) Inventors: Marc Garbey, Houston, TX (US); Albert Huang, Houston, TX (US); Brian James Dunkin, Houston, TX (US); Barbara Lee Bass, Houston, TX (US)

(73) Assignees: University of Houston System, Houston, TX (US); The Methodist Hospital, Houston, TX (US)

( * ) Notice: Subject to any disclaimer, the term of this patent is extended or adjusted under 35 U.S.C. 154(b) by 599 days.

(21) Appl. No.: 14/735,868

(22) Filed: Jun. 10, 2015

(65) Prior Publication Data

US 2015/0374259 A1 Dec. 31, 2015

Related U.S. Application Data

(60) Provisional application No. 62/010,778, filed on Jun. 11, 2014.

(51) Int. Cl.

| | |
|---|---|
| *G06Q 10/06* | (2012.01) |
| *A61B 5/06* | (2006.01) |
| *A61B 5/00* | (2006.01) |
| *A61B 34/20* | (2016.01) |
| *A61B 90/92* | (2016.01) |
| *A61B 90/98* | (2016.01) |

(Continued)

(52) U.S. Cl.
CPC ............ *A61B 5/061* (2013.01); *A61B 5/6889* (2013.01); *A61B 34/20* (2016.02); *A61B 90/92* (2016.02); *A61B 90/98* (2016.02); *G06Q 10/0639* (2013.01); *G06Q 10/06398* (2013.01); *A61B 90/30* (2016.02); *A61B 2034/2057* (2016.02); *A61B 2034/2065* (2016.02); *A61B 2090/065* (2016.02); *A61B 2090/0803* (2016.02); *A61B 2090/0804* (2016.02)

(58) Field of Classification Search
None
See application file for complete search history.

(56) References Cited

U.S. PATENT DOCUMENTS

| | | |
|---|---|---|
| 5,429,142 A | 7/1995 | Szabo et al. |
| 6,302,840 B1 | 10/2001 | Benderev |

(Continued)

FOREIGN PATENT DOCUMENTS

| | | | | |
|---|---|---|---|---|
| WO | WO-2005020835 A1 | * | 3/2005 | ........... A61B 5/0046 |

OTHER PUBLICATIONS

Estebanez, et al. "Maneuvers Recognition in Laparoscopic Surgery: Artificial Neural Network and Hidden Markov Model Approaches." The Fourth IEEE RAS/EMBS International Conference on Biomedical Robotics and Biomechanics. Jun. 24-27, 2012.*

(Continued)

*Primary Examiner* — Susanna M. Diaz
(74) *Attorney, Agent, or Firm* — ParkerHighlander PLLC

(57) ABSTRACT

Systems and methods for monitoring medical procedures. Particular embodiments relate to monitoring medical procedures performed in operating room environments through the use of various types of sensors.

14 Claims, 14 Drawing Sheets

(51) Int. Cl.
*A61B 90/00* (2016.01)
*A61B 90/30* (2016.01)

(56) References Cited

U.S. PATENT DOCUMENTS

| | | | |
|---|---|---|---|
| 7,896,869 B2* | 3/2011 | DiSilvestro | A61B 90/90 128/898 |
| 2004/0254439 A1 | 12/2004 | Fowkes et al. | |
| 2006/0142739 A1* | 6/2006 | DiSilestro | A61B 90/90 606/1 |
| 2006/0166157 A1 | 7/2006 | Rahman et al. | |
| 2007/0282195 A1* | 12/2007 | Masini | A61B 90/36 600/424 |
| 2008/0246610 A1 | 10/2008 | Packert et al. | |
| 2008/0281636 A1 | 11/2008 | Jung et al. | |
| 2010/0157018 A1 | 6/2010 | Lampotang et al. | |
| 2011/0046476 A1 | 2/2011 | Cinquin et al. | |
| 2012/0323501 A1 | 12/2012 | Sarrafzadeh et al. | |
| 2013/0211421 A1* | 8/2013 | Abovitz | A61B 19/2203 606/130 |
| 2013/0332271 A1* | 12/2013 | Hay | G06Q 20/20 705/14.51 |

OTHER PUBLICATIONS

PCT Search Report and Written Opinion issued in International Application No. PCT/US2015/035115, dated Sep. 18, 2015.

* cited by examiner

| Step of Procedure | Event Target | Sensor Type |
|---|---|---|
| Instrument/Back Table Setup | Instrument Racks Placed On Table | Pressure Sensing Strip |
| Patient Brought Into OR | Stretcher Crossing Door Threshold | Pressure Sensing Strip |
| Patient Transferred to OR Table | Patient Weight Transferred From Stretcher to Table | Pressure Sensing Strip |
| Induction of Anesthesia | Ventilation Initiation | Small Motion Detection Camera |
| Operation | First Incision | Scalpel Pick Up Detection |
| Reversal of Anesthesia/Extubate | Ventilator Cessation | Small Motion Detection Camera (Same One As induction of Anesthesia) |
| Patient Transferred to Stretcher | Patient Weight Transferred From Table to Stretcher | Pressure Sensing Strip (Same One As Prior) |
| Patient Taken to Recovery Room | Stretcher Crossing Door Threshold | Pressure Sensing Strip (Same One As Prior) |
| Occupancy of the OR | Movement in the OR | Infrared detector |

FIG. 5

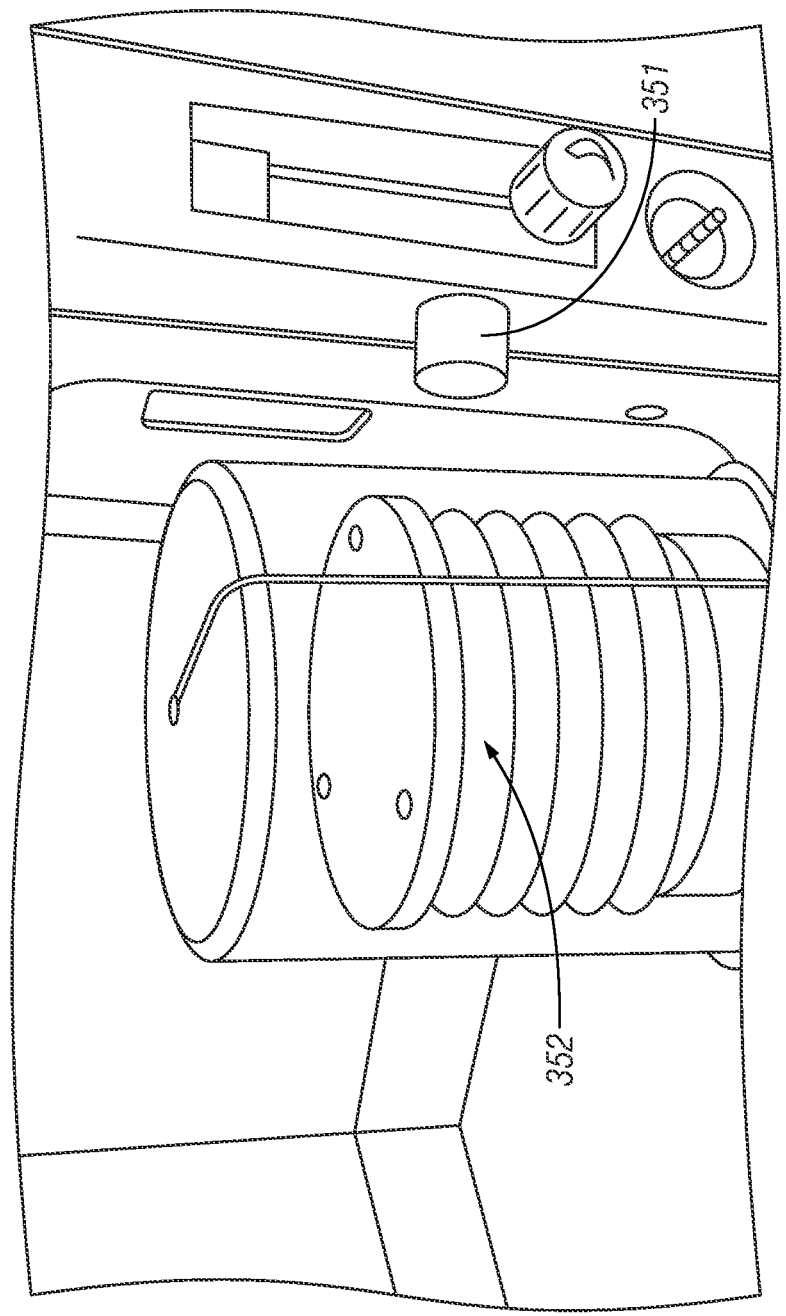

SYSTEMS AND METHODS FOR MEDICAL PROCEDURE MONITORING

CROSS-REFERENCE TO RELATED APPLICATIONS

This application claims priority to U.S. Provisional Patent Application Ser. No. 62/010,778 filed Jun. 11, 2014, the contents of which are incorporated by reference herein.

TECHNICAL FIELD

Exemplary embodiments of the present disclosure relate to systems and methods for monitoring medical procedures. Particular embodiments relate to monitoring medical procedures performed in operating room environments through the use of various types of sensors.

BACKGROUND

Optimum management of multiple hospital operating rooms (OR) is a complex problem. For example, a large hospital such as the Houston Methodist Hospital has approximately seventy active ORs with a large number of procedures per day and per OR that need to be scheduled several weeks in advance. Each procedure requires gathering a team led by a surgeon for a specific block of time in the OR. But even the most standard procedure, such as a laparoscopic cholecystectomy (which account for approximately 600,000 cases per year in the United States), can exhibit a significant variation in time duration. It is often the case that multiple OR scheduling must be done under uncertainties on time duration. Some procedures may lead to fairly unpredictable events, such as unexpected bleeding or additional work that requires more time, and possibly more personnel and equipment. At the same time, physician and patient movement through the perioperative (pre, intra, and post-operative) space directly affects operating room efficiency and timeliness of scheduling.

While the OR is a complex, high technology setting, there is still not an automatic feedback loop between the surgical team and the OR system to allow real time projection, detection, and adjustment of previously made decisions in scheduling. It is believed that effective OR awareness could provide early signs of problems that can allow the OR management to reallocate resources in a more efficient way. Being able to project operating room statuses and patient locations automatically and in real time on a centralized display system will further allow for improved OR management efficiency and efficacy.

A system installed in the OR that has tracking capability of all key events in order to assess the working flow in multiple ORs and builds a statistical model with that data that can be used to rationalize decision making and resource allocation. While there have been numerous works investigating this issue, it seems that there has been no practical solution implemented yet to automatically collect the necessary data for this endeavor.

It has been recognized that OR time is one of the most significant budget expenses in a modern hospital. It is also recognized that delays in OR procedures due to lapses in scheduling and/or OR resources availability have been at least in part responsible for poor surgical outcomes.

Previous investigators (e.g. University of Iowa Prof. Franklin Dexter) have provided an extensive bibliography on OR management under various aspect such as rationale on economics, algorithmic methods to optimize the management, and necessary tools to predict surgery procedure duration. However, such disclosures do not provide systems and methods as disclosed herein utilizing appropriate sensors, modeling, and computer processing implementation. Current OR management software/hardware systems that offer patient and OR status displays rely on manual input of aforementioned statuses.

Previous investigations into OR management optimization typically reviewed OR allocation several days prior to surgery. The input flow of OR procedures to be achieved as well as the resources available (staff, OR, equipment, etc. . . . ) to do the work are assumed to be known. In these investigations, the problem is typically formalized mathematically and solved with some optimization algorithm. In addition, several assumptions are often made on the level of complexity of the problem, depending on the time scale, number of ORs and/or types of surgery. It is assumed that the data available—such as expected time for surgery, patient and staff availability—can be either deterministic or probabilistic with a certain level of uncertainties. In typical previous investigation, the panel of mathematical methods to solve the problem encompasses linear integer programming, petri nets, stochastic optimization, etc. Validation is often based either on simulation tools or true comparison between different methods of scheduling in clinical conditions. However, this work is often based on tedious data acquisition that is done manually, which can be an obstacle to going further and deeper in the OR management field. Exemplary embodiments disclosed herein provide systems and methods to address such issues.

Investigations into predicting OR task durations typically rely on extensive collection of data on OR activities. In such cases, one needs to decide about the level of details used in the description of the procedure, which can result in a statistical model that might be valid for the specific category of intervention only. The reliability of such a statistical model depends on the normalization of the procedure and the quality of service at the hospital. This in turn depends on the standard of the surgical team and might be available only to large volume procedure that offers enough reproducibility.

Prior techniques that have been used to record and annotate the OR activities include a video camera mounted in the light that is above the OR table. In addition, sometimes a fixed video camera may also be mounted on the wall of the OR. For minimally invasive surgery, the video output of the endoscope camera may also be projected and/or recorded. There have been numerous works in computer vision then that either concentrate on following the motion and movements of the surgical team in the OR, or the laparoscopic instrument in the abdominal cavity.

It is also possible to analyze the motion of the hand of the surgeon during the procedure. There is continuous progress made on pattern recognition. It is however, quite difficult to get such methods working with sufficient and consistent accuracy. A primary reason is that there is typically significant variability with in people motion. Tracking a specific event or individual may become unfeasible, due to obstruction of view, or with staff moving in and out of multiple ORs. Accordingly, a computer vision method for OR function tracking is presented with significant obstacles. Exemplary embodiments disclosed herein include systems and method based on distributed sensors to track specific events to address these and other issues.

Previous investigations have also addressed the tracking of OR functions at the surgical tool level. The field of laparoscopic surgery of large volume minimally invasive surgery is one example. In addition, extensive study based on pattern recognition of tools in that view has also been published. Furthermore, radio frequency identification (RFID) tracking of instruments has been a popular solution. However, the OR environment is not favorable to this technology for the tracking of instruments. Similarly, using a bar code on each laparoscopic instrument is also not considered a robust solution.

Therefore, a need in the art exists for a minimally intrusive, yet robust, systems and methods to track perioperative functions that define work flow from the physical as well as cognitive point of view and model perioperative and intraoperative flow to allow efficient multiple OR management scheduling and resource allocation.

SUMMARY OF THE INVENTION

Presented are systems and methods directed to monitor medical procedures and patient/personnel movement and localization. Exemplary embodiments of the present disclosure relate to systems and methods for monitoring medical procedures and patient/personnel movement and localization. Particular embodiments relate to monitoring medical procedures performed in operating room environments and in the perioperative space through the use of various types of sensors.

It is understood that the issues described above for existing systems and methods are merely exemplary and that other deficiencies can be addressed by the exemplary embodiments disclosed herein. While the existing systems and methods issues described above may appear to be readily addressed, there can be cultural barriers that hinder the ability to address such issues. For example, the medical personnel in and around the operating room are typically not versed in the arts used to implement solutions (e.g. sensor technologies and computer arts). Similarly, those versed in the arts used to implement solutions are not typically versed in the issues relating to medical procedures and perioperative patient/personnel movement and localization.

Embodiments of the present disclosure provide systems and methods for non-invasive tracking of perioperative functions that can allow the construction of a powerful statistical model of surgery procedure events to improve scheduling prior to surgery, predict and notify for potential poor outcomes related to perioperative activities, identify perioperative events that are suboptimal, as well as and on-the-fly indicators to revise scheduling in real time and reallocate resources when necessary. Exemplary embodiments can track perioperative functions that define OR work flow and pre and post-operative patient and staff movement in a noninvasive, automatic and real-time way, from the physical as well as cognitive point of view, in addition to modeling OR (and pre and post-operative) flow to allow efficient multiple OR management scheduling and resource allocation.

Exemplary embodiments of methods disclosed herein can comprise one or more of the following steps: (i) identify the macro steps in perioperative flow that are important to multiple OR system management; (ii) associate with each step a noninvasive redundant and robust sensing mechanism that accurately tracks locations and events; and (iii) generate a mathematical model of OR management that is amenable to optimum scheduling and resource allocation methods. Diagnostic data from the signal time series can provide a broad variety of information, including for example, time lapse when OR system is not used, time lapse when coordination, staff or equipment resource is lacking, and outliers on anesthesia/surgery time. Exemplary embodiments disclosed herein utilize an agile development procedure that alternates design, testing, and user feedback. In this process, choices made on steps (i) and (ii) are revisited to get improved diagnostic data.

Exemplary embodiments include a medical procedure monitoring system comprising a computer readable medium comprising a plurality of standards for a medical procedure, and comprising a plurality of sensors, and a computer processor. In specific embodiments, each sensor is configured to: detect a parameter of a component used in the medical procedure; and provide an output based on the parameter of the component detected. In particular embodiments, the computer processor is configured to: receive the output from each sensor; and compare the output from each sensor to a standard from the plurality of standards for the medical procedure.

In certain embodiments, the computer processor is configured to alter the plurality of standards for the medical procedure after receiving the output from each sensor. In particular embodiments, the computer processor is configured to alter the plurality of standards for the medical procedure after receiving the output from each sensor via a mathematical model. In some embodiments, the output provided by each sensor is a binary output. In specific embodiments, the plurality of sensors are located in an operating room. In certain embodiments, the plurality of sensors are sealed from an atmospheric environment in the operating room. In particular embodiments, the plurality of sensors comprises a light brightness sensor. In specific embodiments, the plurality of sensors comprises force-sensing resistor strips. In some embodiments, the plurality of sensors comprises a force-sensing resistor panel. In certain embodiments, the plurality of sensors comprises a split core current sensor. In particular embodiments, the plurality of sensors comprises a video camera. In specific embodiments, the video camera is directed to a ventilator to detect movement of a bellows. In some embodiments, the video camera is directed to detect a specific color, and/or changes in ambient light intensity. In certain embodiments, the changes in ambient light intensity indicate a differentiation between open and minimally invasive procedures. In particular embodiments, the plurality of sensors comprise radio frequency identification (RFID) sensors to capture personnel movement in a perioperative space. In some embodiments, the system is configured to detect the parameter of the component used in the medical procedure and provide the output based on the parameter of the component detected in real-time.

Exemplary embodiments include a method for monitoring a medical procedure, the method comprising: detecting with a sensor a parameter of a component used in the medical procedure; providing an output from the sensor based on the parameter of the component detected; receiving the output from each sensor with a computer processor; reading a computer readable medium comprising a plurality of standards for a medical procedure; and comparing the output from each sensor to a standard from the plurality of standards for the medical procedure.

Certain embodiments further comprise altering the plurality of standards for the medical procedure after receiving the output from each sensor. Particular embodiments further comprise altering the plurality of standards for the medical procedure after receiving the output from each sensor via a mathematical model. In some embodiments, the output provided by each sensor is a binary output. In specific embodiments, the plurality of sensors is located in an operating room. In certain embodiments, the plurality of sensors is sealed from an atmospheric environment in the operating room. In particular embodiments, the plurality of sensors comprises a light brightness sensor, and in some embodiments the light brightness sensor is configured to detect changes in ambient light intensity. In specific embodiments, the changes in ambient light intensity indicate a differentiation between open and minimally invasive procedures. In certain embodiments, the plurality of sensors comprises force-sensing resistor strips. In particular embodiments, the plurality of sensors comprises a force-sensing resistor panel. In some embodiments, the plurality of sensors comprises a split core current sensor. In specific embodiments, the plurality of sensors comprises a video camera. In certain embodiments, the video camera is directed to a ventilator to detect movement of a bellows. In particular embodiments, the video camera is directed to detect a specific color. In some embodiments, the sensor comprises a radio frequency identification (RFID) sensor to capture personnel movement in a perioperative space. In specific embodiments, each of the steps of the method are performed in real time.

The details of one or more embodiments of the invention are set forth in the accompanying drawings and the description below.

Certain terminology is used in the following description are for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

Exemplary embodiments of the present disclosure are provided in the following drawings. The drawings are merely examples to illustrate the structure of exemplary devices and certain features that may be used singularly or in combination with other features. The invention should not be limited to the examples shown.

FIG. 5 is a table corresponding procedural events and sensor types configured for monitoring by the embodiment of FIG. 1 and the associated outputs of such components;

FIG. 11 is an illustration of a ventilator status sensor configured for use with the embodiment of FIG. 1;

DETAILED DESCRIPTION

Figure 1:
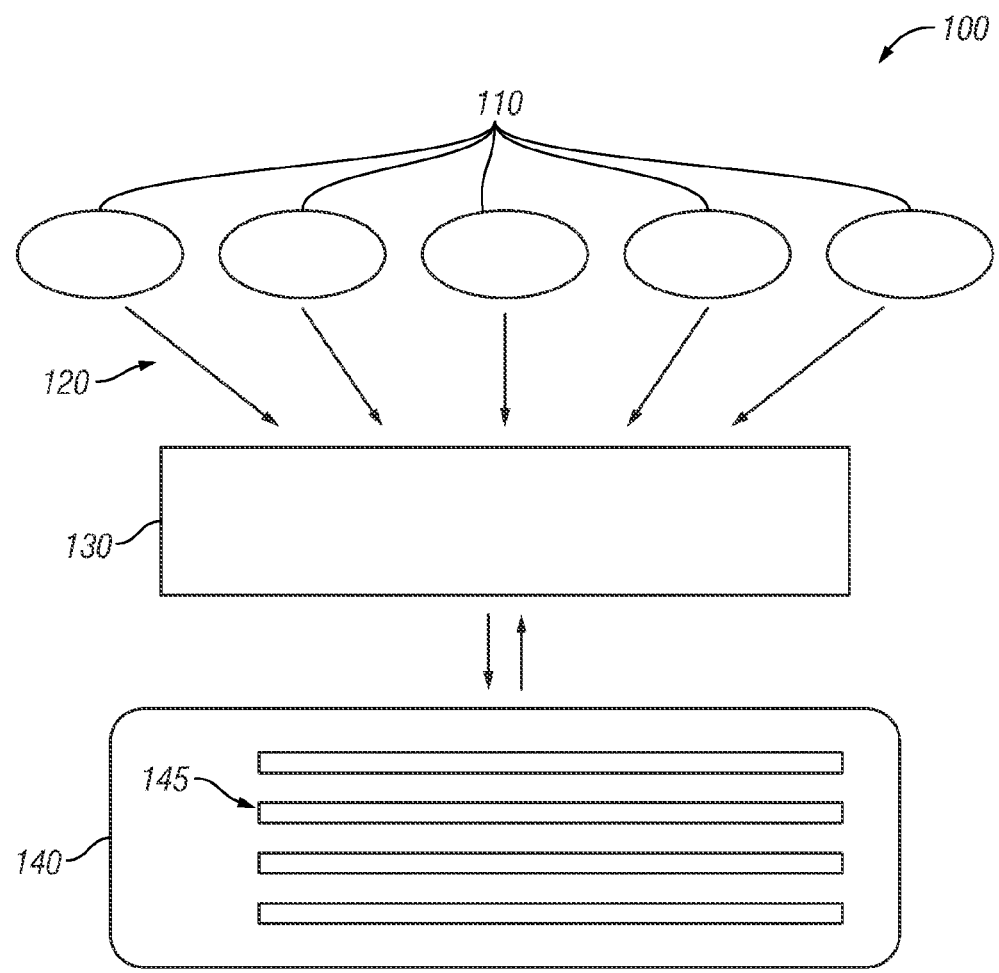
FIG. 1 is a schematic diagram of an exemplary embodiment of a system according to the present disclosure.
Figure 2:
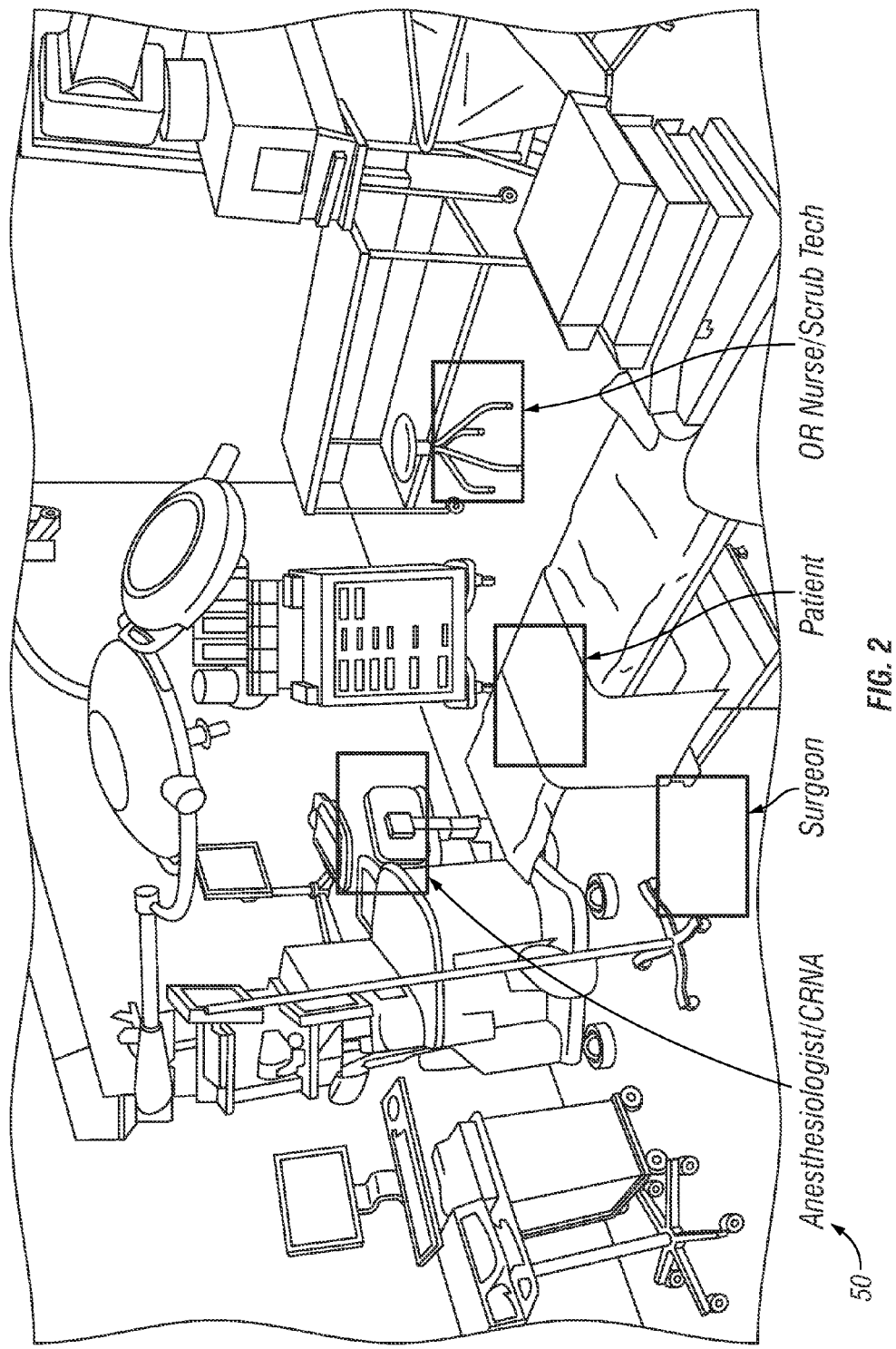
FIG. 2 is a perspective view of an operating room configured for use with the embodiment of FIG. 1.

Referring initially to FIGS. 1-2 a schematic of a system 100 configured for medical procedure monitoring is displayed along with an operating room 50 configured for use with system 100. In the embodiment shown, system 100 comprises a plurality of sensors 110 configured to detect a parameter of a component used in a medical procedure (e.g., a procedure performed in operating room 50). As explained in further detail below, sensors 110 may be configured to detect many different types of parameters, including for example, a component position, operating state, movement, color, or other parameter. As used herein, the term "component" is interpreted broadly to include any device, person or object used in or around a medical procedure. Examples of components include medical instruments used to directly perform the medical procedure (e.g. scalpels, forceps, catheters, etc.), personnel (patient, surgeon, nurse, anesthesiologist, etc.), and peripheral devices associated with the medical procedure (operating room entry door, draping around patient, etc.)

In exemplary embodiments, sensors 110 can be configured to provide an output 120 based on the parameter of the component detected. In specific embodiments, computer processor 130 is configured to communicate with a computer readable medium 140 comprising a plurality of parameters 145 in and around a medical procedure. In exemplary embodiments, system 100 may alter the plurality of parameters 145 in and around a medical procedure (e.g. via a mathematical model) after receiving outputs 120 from each sensor. In particular embodiments, sensors 110 can provide a binary output (based on the detected parameter) to a computer processor 130 configured to receive output 120 from sensors 110.

Figure 3:
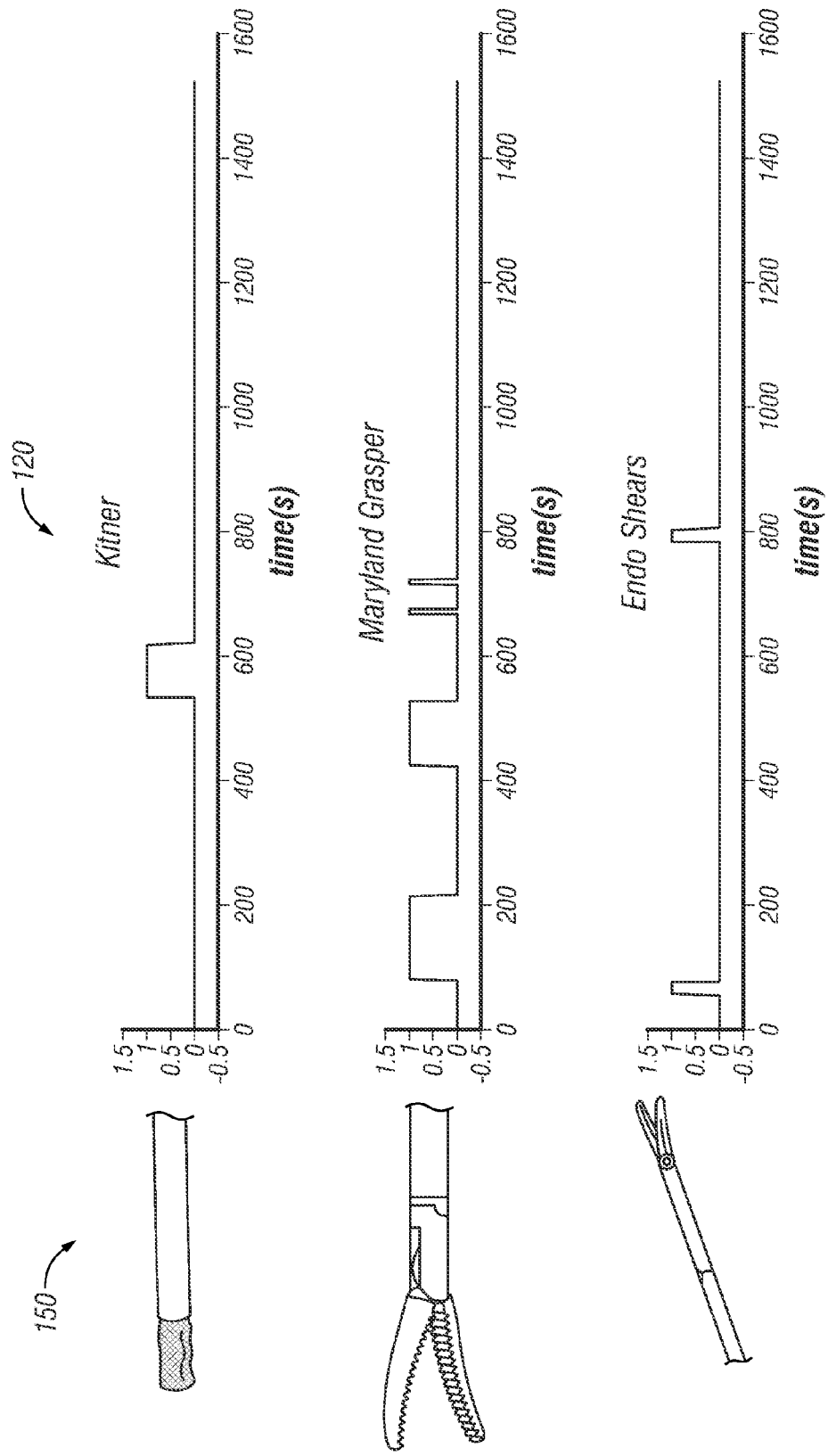
FIG. 3 is a table corresponding components configured for monitoring by the embodiment of FIG. 1 and the associated outputs of such components.
Figure 3:
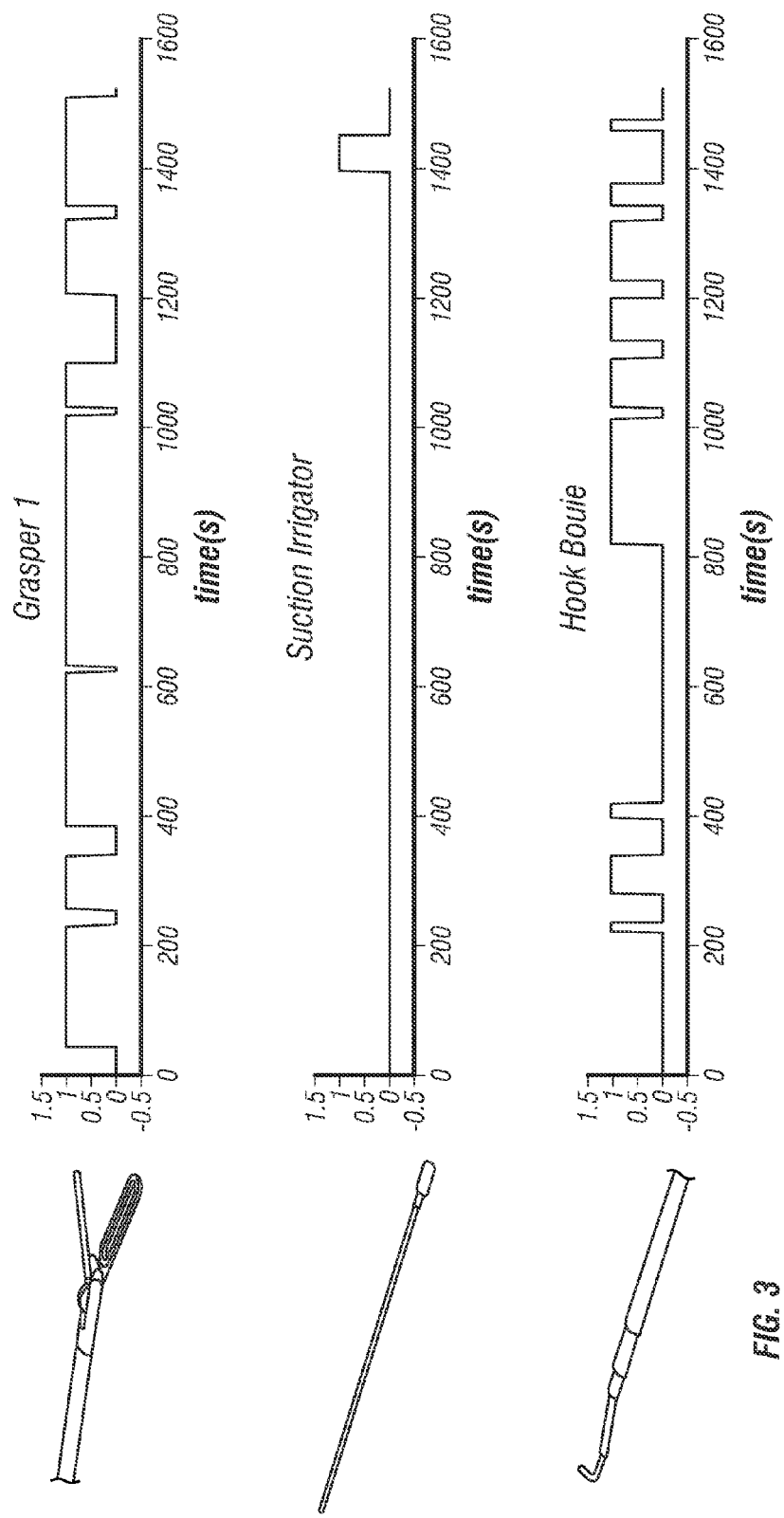
Figure 3:
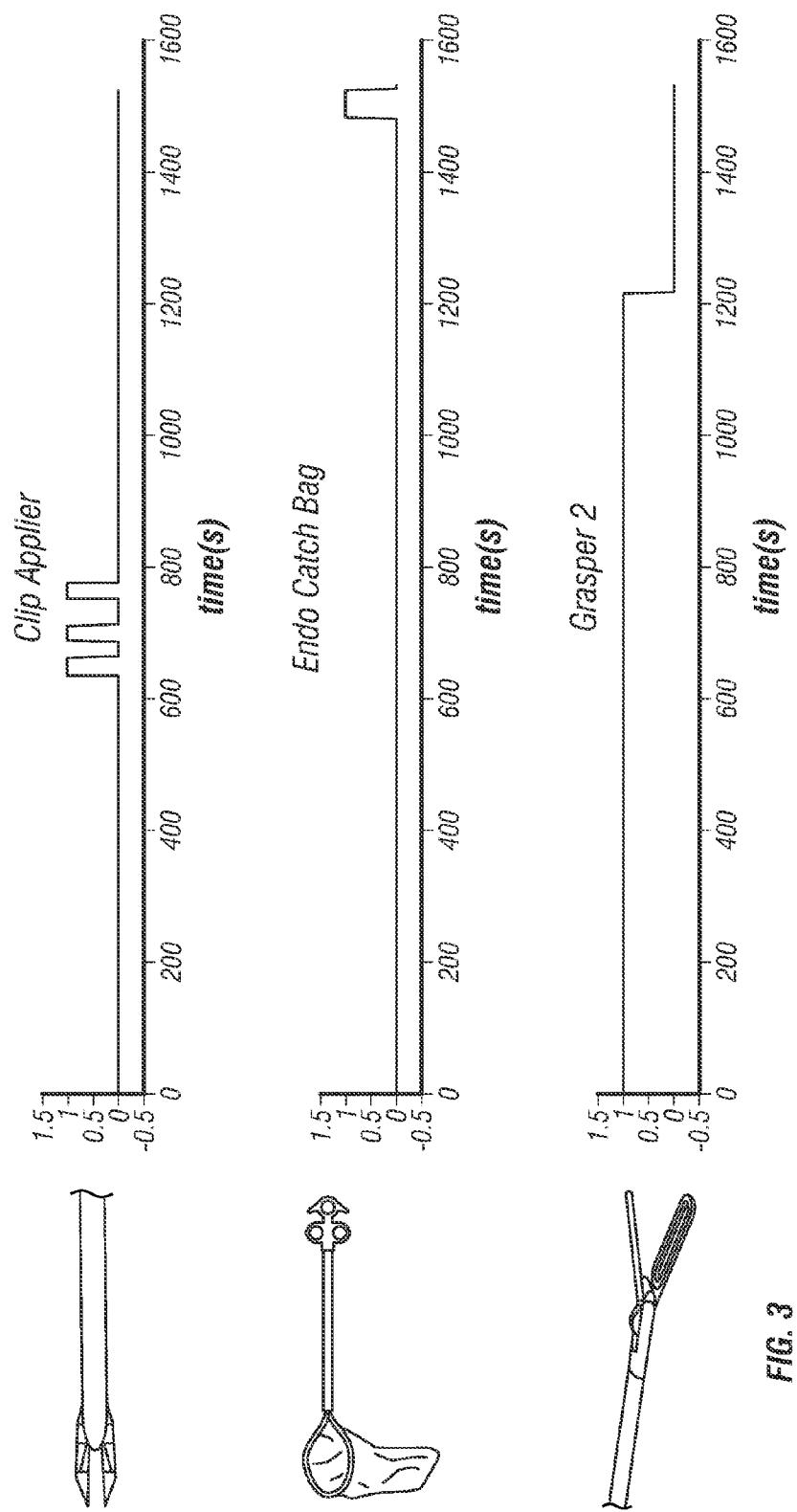
Figure 4:
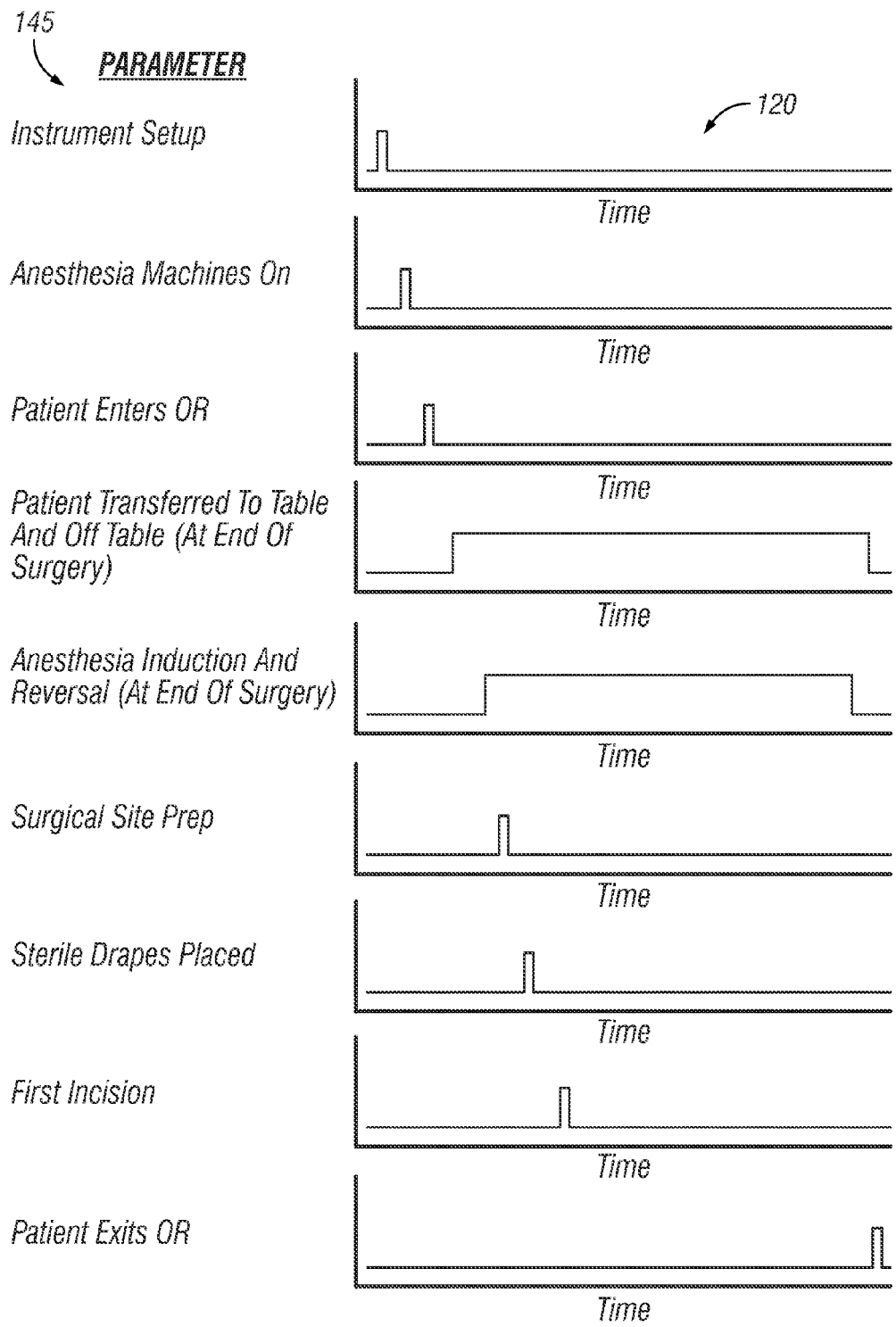
FIG. 4 is a table corresponding events or parameters binary outputs of associated sensors configured for use in the embodiment of FIG. 1.

Referring now to FIG. 3, a plurality of components 150 are illustrated beside a corresponding binary output 120 that is indicative of a condition of the component 150. FIG. 4 provides an example of various events or parameters 145 of an exemplary medical procedure and binary outputs 120 of sensors used to detect the events/parameters over time. For example, sensors detecting instrument setup, anesthesia machine operational status and patient entry to the operating room provide a binary discrete output prior to the patient being transferred to the operating table. Sensors detecting the patient's location on the operating room table, changes to the OR's ambient light intensity, and anesthesia induction and reversal provide a discrete positive output during the procedure. These two sensor outputs also overlap sensor outputs for surgical site preparation, placement of sterile drapes, and first incision. The final sensor output for the patient exiting the operating room indicates the conclusion of the procedure.

Figure 6:
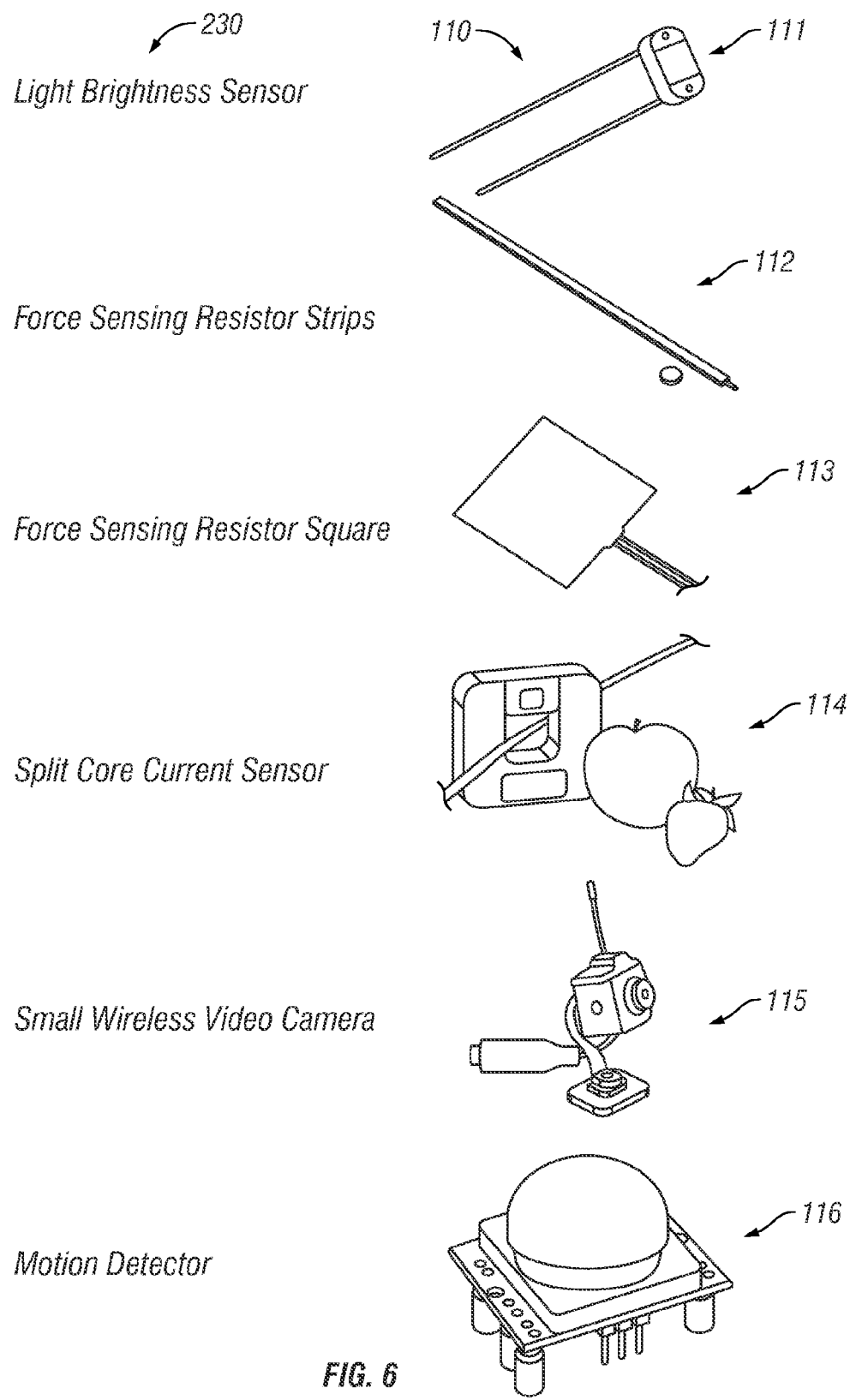
FIG. 6 provides illustrations of sensor types for various sensors configured for use with the embodiment of FIG. 1.
Figure 7:
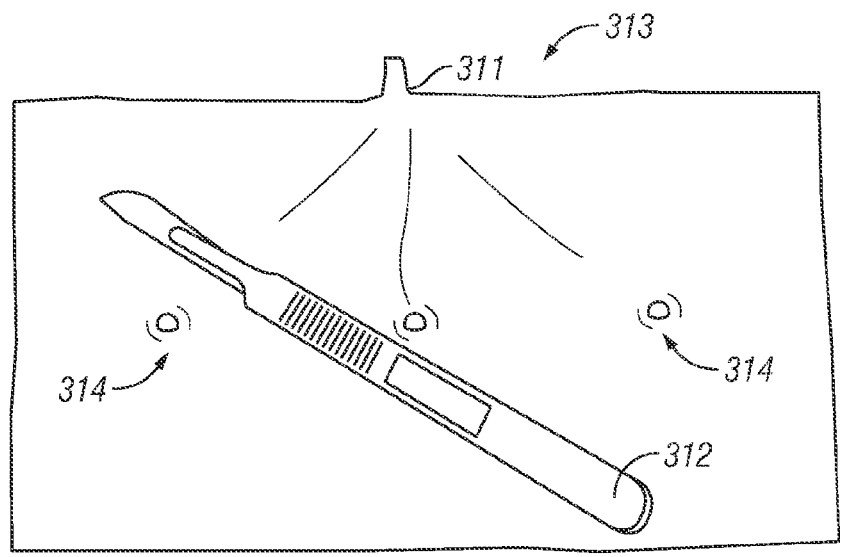
FIG. 7 is an illustration of a light sensor configured for use with the embodiment of FIG. 1.

As shown in FIG. 5, a table 200 provides a list of procedure steps 210 (e.g. corresponding to specific standards or parameters 145) in an exemplary medical procedure. In addition, table 200 provides a corresponding list of event targets 220 (e.g. corresponding to outputs 120 for individual sensors 110) and sensor types 230 for various sensors 110. FIG. 6 also provides illustrations of various sensor types (or modalities) 230 for various sensors 110, including a light brightness sensor 111, a force-sensing resistor strip 112, a force-sensing resistor panel 113, a split core current sensor 114, a video camera 115, and a motion sensor 116. It is understood that the provided lists and sensor types are merely exemplary, and that other steps, event targets, and sensor types may be used in other embodiments.

Referring now to FIGS. 7-14, various exemplary embodiments of sensors and their locations are provided. For example, in FIG. 7 a light sensor 311 can be used to detect when a scalpel 312 is removed from a surface 313 (e.g. an instrument table). In a particular embodiment, light sensor 311 may detect light when scalpel 312 is removed from surface 313 to indicate that the instrument is in use. When scalpel 312 is placed back onto the surface 313, light can be blocked from light sensor 311 and sensor 311 can provide an output that scalpel 312 is in a stored location on surface 313 and not in use. In particular embodiments, lights 314 (e.g. LEDs) can be used to indicate the proper position on surface 313 for scalpel 312 to be placed when not in use. In the embodiment shown, a single dedicated small light sensor can be used to detect when the scalpel is taken off a table for the first incision. For example, two red LEDs on either side of the sensor can light up the sensor location for accurate scalpel positioning when setting up an instrument table for a surgical case. The LEDs can be placed underneath a drape and the light sensor placed between LEDs and beneath the drape.

Figure 8:
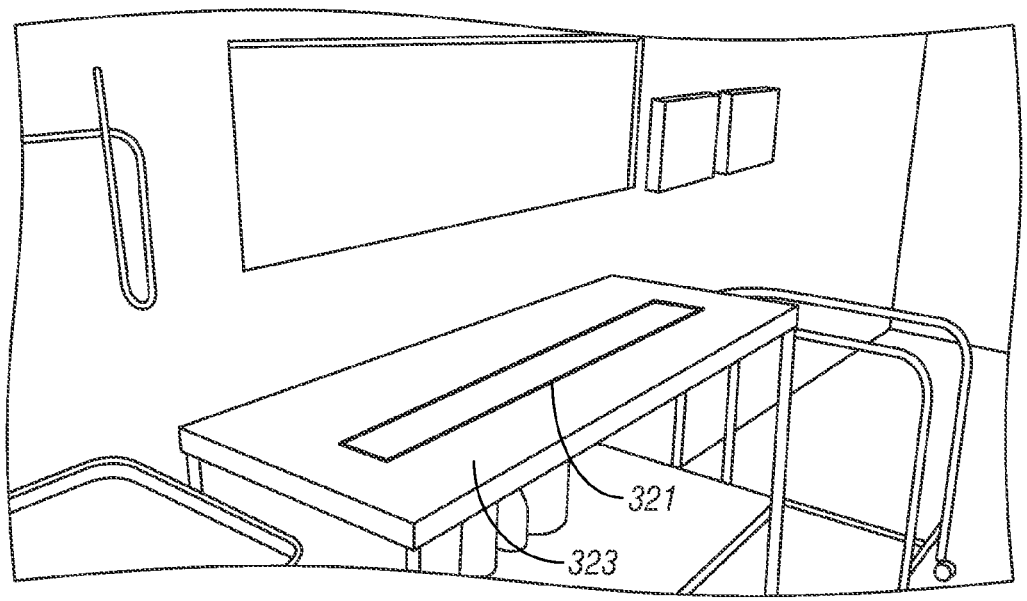
FIG. 8 is an illustration of instrument detection sensor configured for use with the embodiment of FIG. 1.
Figure 10:
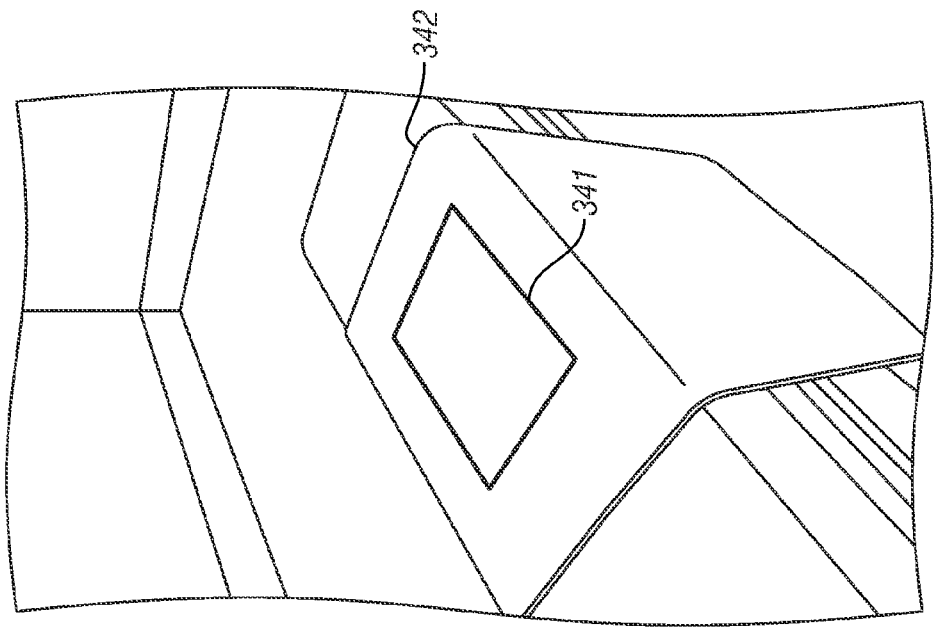
FIG. 10 is an illustration of a patient transfer detection sensor configured for use with the embodiment of FIG. 1.
Figure 9:
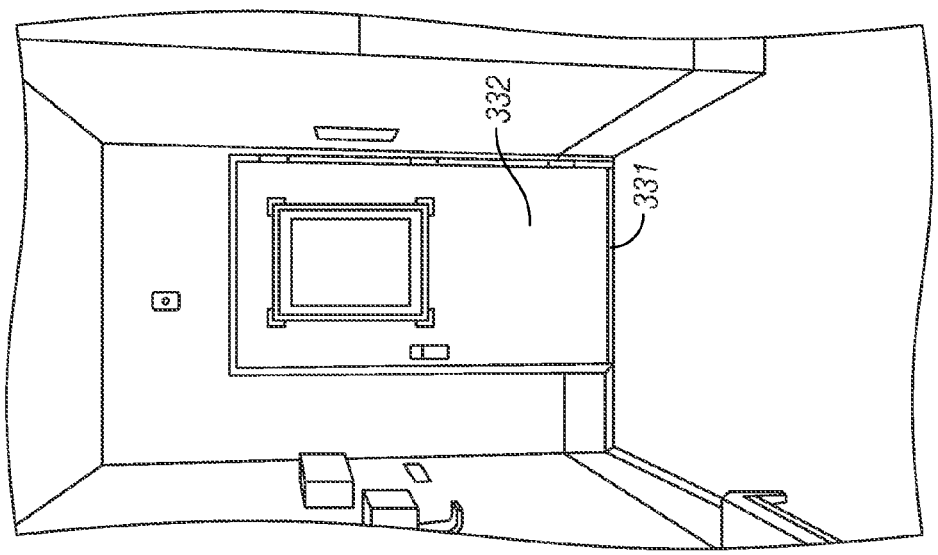
FIG. 9 is an illustration of a patient entry detection sensor configured for use with the embodiment of FIG. 1.

Referring now to FIG. 8, a sensor 321 may be configured as a thin, low profile pressure sensitive strip on surface 323 (e.g. an instrument table). In exemplary embodiments, sensor 321 can detect whether or not an instrument or component is located on surface 323 by the weight of the various instruments or components placed on the surface. As shown in FIG. 9, a sensor 331 may detect when a patient gurney crosses the operating room threshold for entry door 332 to enter or exit the operating room environment. In particular embodiments, sensor 331 may configured as a floor-installed tape-style sensor strip. In specific embodiments a sensor strip can detect the wheels of the patient's bed to record when the patient is in the room. The same sensor can also detect when the patient has left the operating room after the operation. Referring now to FIG. 10, a sensor 341 can be configured as a pressure sensor (e.g. a force-sensing resistor panel) to detect when a patient has been transferred to or from an operating room table 342. In particular embodiments, sensor 341 can be configured as a small flat pressure sensor that can detect the weight of the patient upon transfer from the gurney before the operation and detect that the patient is no longer on the bed at the end of the operation.

Figure 12:
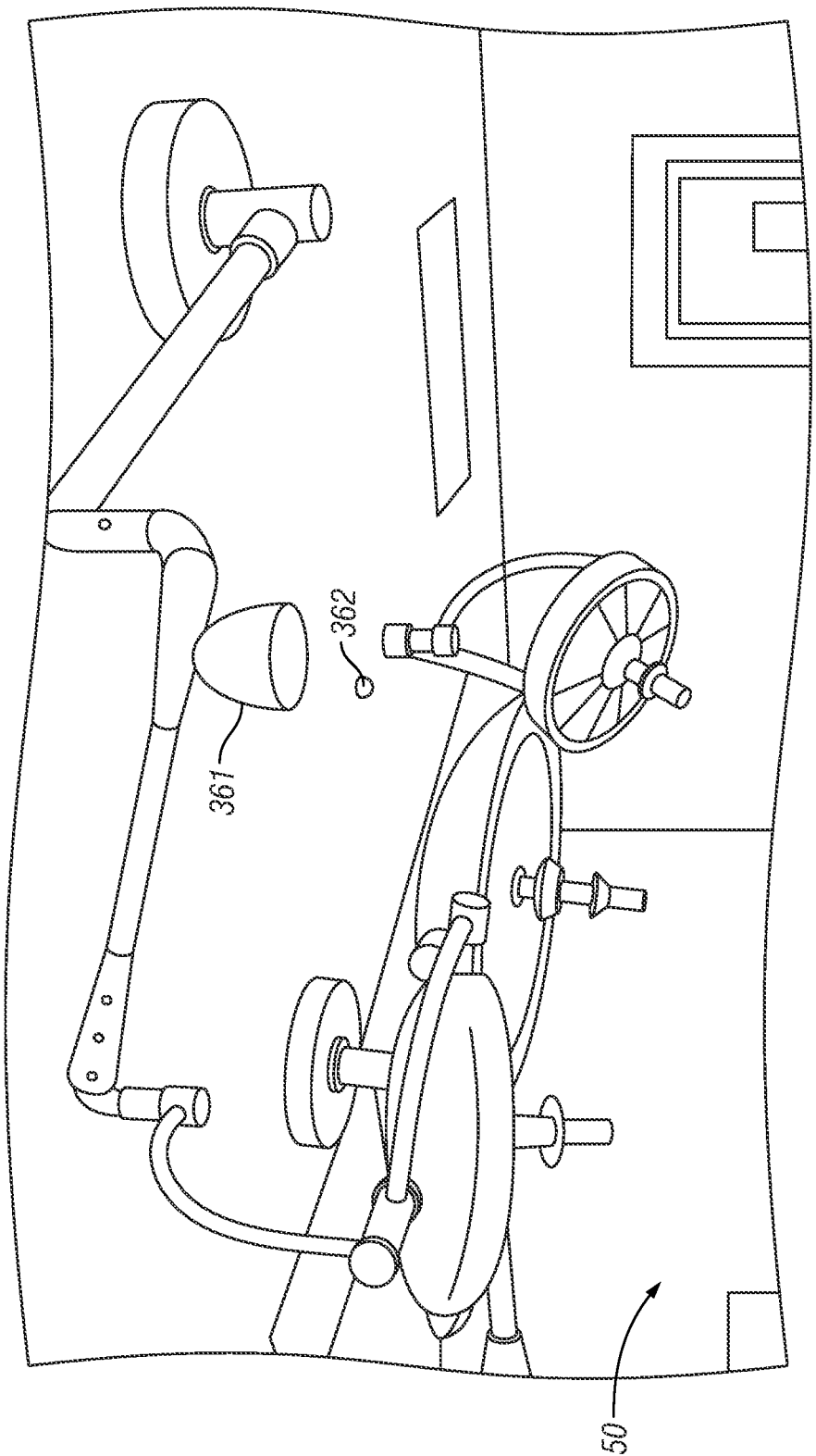
FIG. 12 is an illustration of a video detection sensor configured for use with the embodiment of FIG. 1.
Figure 13:
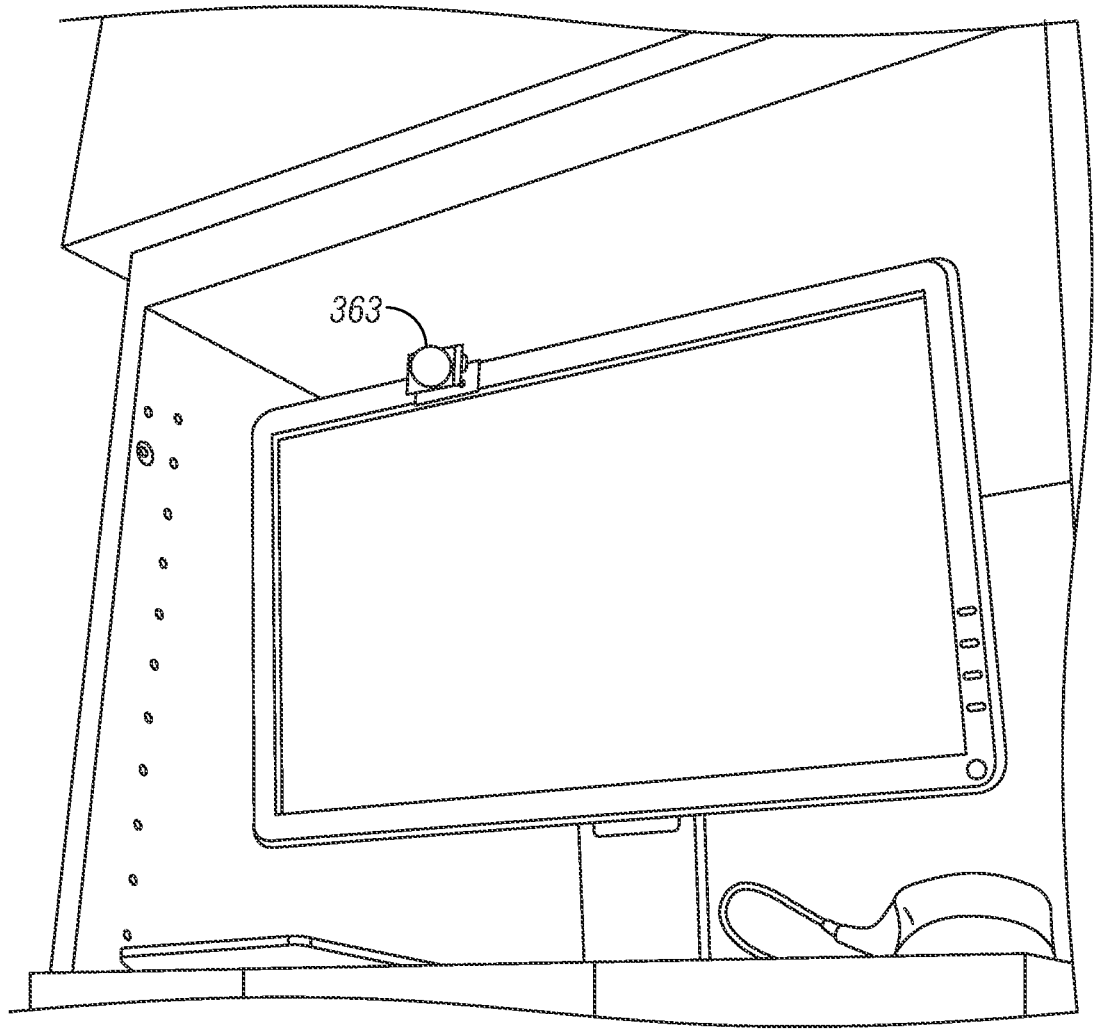
FIG. 13 is an illustration of a motion detector sensor configured for use with the embodiment of FIG. 1.
Figure 14:
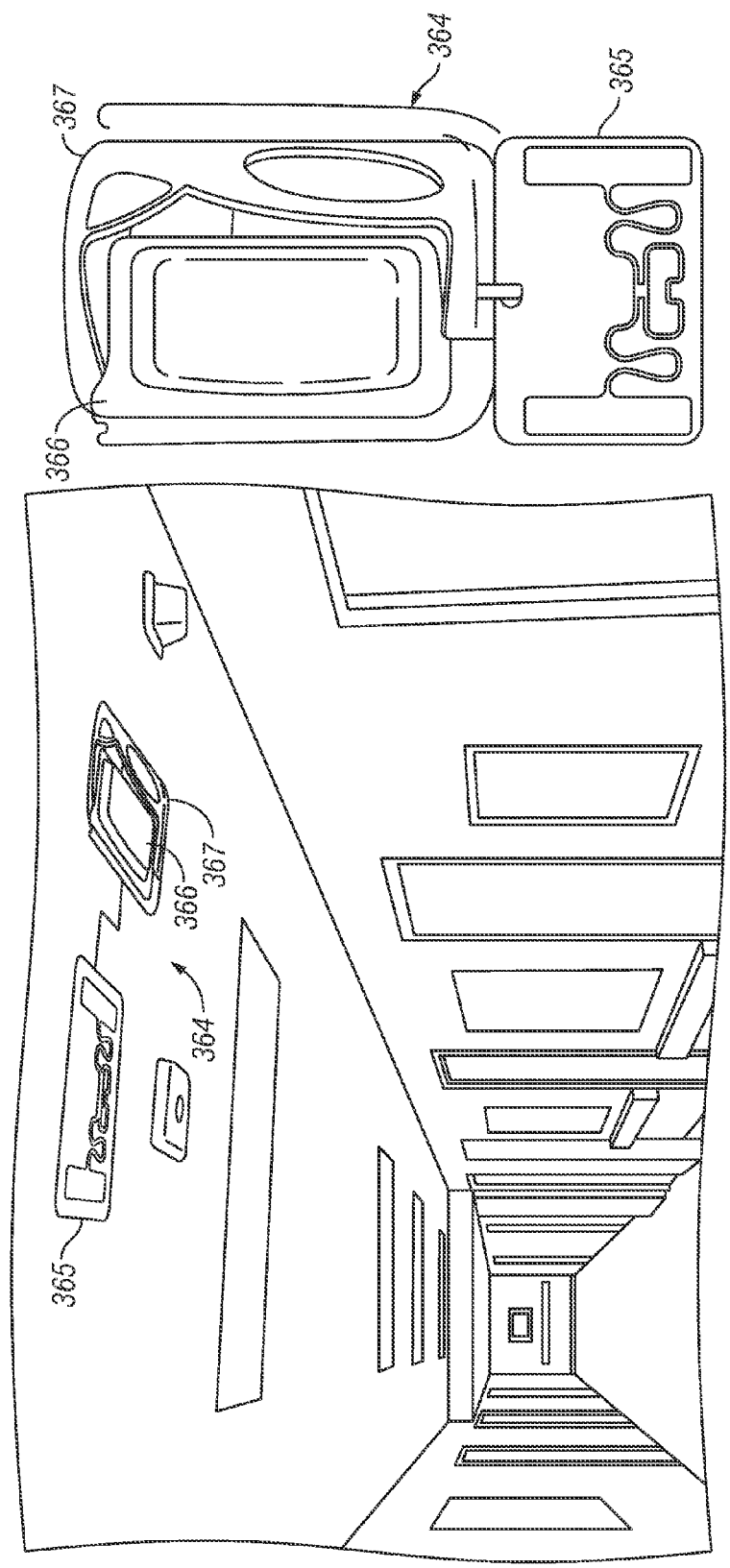
FIG. 14 is an illustration of a RFID tag and sensor system configured for use with the embodiment of FIG. 1.

As shown in FIG. 11, a sensor 351 can provide an output to indicate a ventilator 352 is active or inactive. In particular embodiments, sensor 351 may be configured as a video camera configured to detect motion of a bellows in ventilator 352 as well as ambient light in the operating room potentially signifying a change in the status of the procedure (e.g. progression to a minimally invasive portion of the operation where the ambient lights in the OR are traditionally dimmed). The active/inactive status of ventilator 352 can be used to determine if the patient is currently intubated and being ventilated. Sensor 351 can also detect ventilator 352 has stopped, signaling extubation and an end of the procedure. Referring now to FIG. 12, a sensor 361 can be mounted to a ceiling 362 of operating room 50 environment and configured to detect one or more particular colors associated with a specific step of the medical procedure being performed. For example, sensor 361 may be a video camera configured to detect a blue color to indicate that draping has been placed around the patient. In addition, sensor 361 may be configured to detect an orange-brown color to indicate that sterilization solution has been applied to the patient. In FIG. 13, an example of a general motion sensor 363 placed in the OR is provided. Sensor 363 may be used in conjunction with data from the complement of sensors to determine the status of the operating room (occupied vs. not occupied etc.). Finally, in FIG. 14, an example of a RFID sensor system 364 is shown comprising an antenna 365, an RFID reader 366 and a PC 367. Sensor system 364 can be integrated into the sensor array so that a centralized computer can capture staff movement and location in real time for appropriate perioperative planning and management.

The above examples of sensors are not intended to be an exhaustive list of the types of sensors that may be used in exemplary embodiments of the present disclosure. In general, sensors in exemplary embodiments may target a specific event, require minimal post-processing, and provide a binary outcome (e.g. "yes/no" for a time event occurrence). Other considerations for sensor selection may include equipment cost and ease of installation (e.g. minimal wiring and no specific sterilization requirements). Still other considerations may include a lack of interference or intrusion with OR equipment and surgical team functions.

Referring back now to FIG. 1, in specific embodiments, computer processor 130 can be configured to communicate with a computer readable medium 130 comprising a plurality of standards 140 for a medical procedure. In exemplary embodiments, system 100 may alter the plurality of standards 140 for the medical procedure (e.g. via a mathematical model) after receiving outputs 120 from each sensor.

In exemplary embodiments, the mathematical model can be developed in conjunction with overall tracking of the OR functions, which provides systematically with no human intervention, an n-uplet $(T_1, T_2, \ldots, T_n)$ of positive real numbers for each procedure. $T_j$ (j=1 ... n), represents the time at which each specific targeted event (e.g. those listed in FIG. 5) occurs. The number n of targeted tasks is for example eleven in FIG. 5, and can be adjusted on demand for the surgery application.

Exemplary embodiments of the system disclosed herein are designed to provide robust and accurate data $T_j$, since each task is tracked by a specific sensor designed for it. (T1, ..., Tn) represent the time portrait of the surgery procedure, which is a measure of the procedure performance. The average cost of every minute in the OR is approximately $100. This time portrait provides also information on which task interval may take too long.

Exemplary embodiments register the time portrait of each surgery occurring in a given OR, which provides a large data set amenable to standard data mining techniques. For example, clustering these n-uplet in the n dimensional space can rigorously separate standard performance from others with respect to its time portrait. It can also allow computation of the average standard time portrait of a standard procedure and the dispersion around this standard. In addition, it can allow one to automatically classify procedures that are nonstandard into groups and to measure the distance between standard and nonstandard groups to assess economical impact.

One can also look in more details at the relative importance of each events and there interdependency with a principle component analysis. It is also possible to provide the minimum subset of task that provide the same clustering than the original time portrait and therefore target the marker of inefficiency. Furthermore, a database of time portrait can be correlated to the data base of patient outcome after surgery. A main source of information is the National Surgical Quality Improvement Program—http://site.acsn-sqip.org which is a rigorous multi-parameter correlation analysis of patient outcomes that can also provide which combination of tasks has maximum impact on quality or failures, such as surgical site infection.

Embodiments disclosed herein provide a low cost system that does not require new techniques or responsibilities from the surgeon or medical personnel. In addition, the systems and methods are robust and accurate, and can be installed in a standard operating environment. The system also does not present additional risks to patients.

It is understood that the methods and mathematical models described in the sections below are exemplary of one embodiment, and that other embodiments are contemplated in this disclosure.

\*\*\*

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

REFERENCES

The contents of the following references are incorporated by reference herein:

Abouleish A, et al., "Labor Costs Incurred by Anesthesiology Groups Because of Operating Rooms Not Being Allocated and Cases Not Being Scheduled Maximize Operating Room Efficiency." Anesth Analg 2003; 96: 1109-13.

Agarwal S, Joshi A, Finin T, Yesha Y, "A Pervasive Computing System for the Operating Room of the Future." Mobile Networks and Applications. 2007; 12:215-28.

Alarcon A and Berguer R, "A comparison of operating room crowding between open and laparoscopic operations." Surgical Endoscopy 1996; 10(9):916-19.

Allan M, Ourselin, S, Thompson S, Hawkes D J, Kelly J and Stoyanov D, "Toward detection and localization of instruments in minimally invasive surgery," IEEE Transactions on Bio-medical Engineering, April 2013.

Avery D M III and Matullo K S, "The efficiency of a dedicated staff on operating room turnover time in hand surgery," The Journal of Hand Surgery 39:108-110, 2014.

Banditori C, Cappanera P, Visintin F, "A combined optimization-simulation approach to the master surgical scheduling problem. IMA Journal of Management Mathematics 24:155-187, 2013.

Bardram J. E., Doryab A., Jensen R. M., Lange P. M., Nielsen K. L. G., and Petersen S. T., "Phase recognition during surgical procedures using embedded and body-worn sensors." pp. 45-53.

Blasinski H, Nishikawa A, Miyazaki F., "The application of adaptive filters for motion prediction in visually tracked laparoscopic surgery." Paper presented at: Robotics and Biomimetics, 2007. ROBIO 2007. IEEE International Conference on; 15-18 Dec. 2007, 2007.

Blum T, Padoy N, Feussner H, and Navab N, "Modeling and online recognition of surgical phases using Hidden Markov Models," Med Image Comput Comput Assist Interv, vol. 11, no. Pt 2, pp. 627-35, 2008.

Bouarfa L, Jonker P P and Dankelman J, "Discovery of high-level tasks in the operating room, Journal of Biomedical Informatics," In Press, DOI: 10.1016/j.jbi.2010.01.004.

Carey K, Burgess J F Jr and Young G J, "Hospital competition and financial performance: the effects of ambulatory surgery centers." Health Economics 20:571-581, 2011.

Choi S and Wilhelm W E, "On capacity allocation for operating rooms," Computers and Operations Research 44:174-184, 2014.

Climent J and Mares P, "Real-time tracking system for assisted surgical operations. Latin America Transactions," IEEE (Revista IEEE America Latina). 2003; 1(1):8-14.

Colombo J. R., Jr., Haber G. P., Rubinstein M., and Gill I. S., "Laparoscopic surgery in urological oncology: brief overview," Int Braz J Urol, 5, pp. 504-12, Brazil, 2006.

Denton B T, Miller A J, Balasubramanian H J, Huschka T R, "Optimal allocation of Surgery Blocks to Operating Rooms under Uncertainty," Operation Research 58, 2010, pp 802-816.

Dexter F, et al., "Use of Operating Room Information System Data to Predict the Impact of Reducing Turnover Times on Staffing Costs.' Anesth Analy 2003; 97:1119-26.

Dexter F, Macaro A and O'Neill L, Scheduling surgical cases into overflow block time-computer simulation of the effects of scheduling strategies on operating room labor costs, Anesth Analg 2000, 90 (4) 980-8.

Dexter F, Willemsen-Dunlap A, and Lee J, "Operating Room Managerial Decision-Making on the Day of Surgery with and without Computer Recommendations and Status Displays." Anesth Analg 2007; 105:419-29.

Doryab A, and Bardram J E, "Designing activity-aware recommender systems for operating rooms," in Proceedings of the 2011 Workshop on Contextawareness in Retrieval and Recommendation (CaRR '11), New York, N.Y., USA, 2011, pp. 43-46.

Doryab A, Togelius J, and Bardram J, "Activity-aware recommendation for collaborative work in operating rooms," in Proceedings of the 2012 ACM international conference on Intelligent User Interfaces (IUI '12), New York, N.Y., USA, 2012, pp. 301-304.

Durucan E and Ebrahimi T, "Change Detection and Background Extraction by Linear Algebra," Invited Paper Proceedings of the IEEE, Vol 89, No 10, October 2001.

Dutkiewicz P, Kielczewski M, Kowalski M. Visual tracking of surgical tools for laparoscopic surgery. Paper presented at: Robot Motion and Control, 2004. RoMoCo '04. Proceedings of the Fourth International Workshop on; 17-20 Jun. 2004, 2004.

Dutkiewicz P, Kietczewski M, Kowalski M, Wroblewski W. Experimental verification of visual tracking of surgical tools. Paper presented at: Robot Motion and Control, 2005. RoMoCo '05. Proceedings of the Fifth International Workshop on; 23-25 Jun. 2005, 2005.

Estebanez, B, del Saz-Orozco P, Rivas I, Bauzano, E, Muoz, V. F. and Garcia-Morales, I., "Maneuvers recognition in laparoscopic surgery: Artificial Neural Network and hidden Markov model approaches," 4th IEEE RAS & EMBS International Conference on Biomedical Robotics and Biomechatronics, pp 1164-1169, 24-27 Jun. 2012.

Fry D E, Pine M, Jones B L, Meimban R J., "The impact of ineffective and inefficient care on the excess costs of elective surgical procedures." Journal of American College of Surgeons 212:779-786, 2011.

Helmreich R, Davies J. 3 Human Factors in the Operating Room: Interpersonal Determinants of Safety, Efficiency, and Morale. Balliere's Clinical Anaesthesiology. Vol 10, Issue 2 1996, pp 277-295.

Herron D., Gagner M., Kenyon T., and Swanstrom L., "The minimally invasive surgical suite enters the 21st century," Surgical Endoscopy, vol. 15, no. 4, pp. 415-422, 2001.

Kodali B S, Kim K D, Flanagan H, Ehrenfeld J M, Urman R D., "Variability of subspecialty-specific anesthesia-controlled times at two academic institutions." Journal of Medical Systems 38:11, 2014.

Kranzfelder M., Schneider A., Blahusch G., Schaaf H., and Feussner H., "Feasibility of opto-electronic surgical instrument identification," Minim Invasive Ther Allied Technol, 5, pp. 253-8, England, 2009.

Liu C. C., Chang C. H., Su M. C., Chu H. T., Hung S. H., Wong J. M., and Wang P. C., "RFID-initiated workflow control to facilitate patient safety and utilization efficiency in operation theater," Comput Methods Programs Biomed, 3, pp. 435-42, Ireland: A 2010 Elsevier Ireland Ltd, 2011.

Liu C C, Chang C H, Su M C, Chu H T, Hung S H, Wong J M, et al. "RFID-initiated workflow control to facilitate patient safety and utilization efficiency in operation theater." Comput Methods Programs Biomed. 2011; 104(3):435-42.

Macario, Alex., "Are You Hospital Operating Rooms "Efficient"?," Anesthesiology 2006; 105:237-40.

Marjamaa R., Vakkuri A., and Kirvel O., "Operating room management: why, how and by whom?," Acta Anaesthesiologica Scandinavica, vol. 52, no. 5, pp. 596-600, 2008.

Meskens N, Duvivier D, Hanset A., "Multi-objective operating room scheduling considering desiderata of the surgical team." Decision Support Systems 55:650-659, 2013 References on Impact of OR Management on finance, staffing and surgical outcome.

Nakamoto M, Nakada K, Sato Y, Konishi K, Hashizume M, Tamura S. Intraoperative Magnetic Tracker Calibration Using a Magneto-Optic Hybrid Tracker for 3-D Ultrasound-Based Navigation in Laparoscopic Surgery. Medical Imaging, IEEE Transactions on. 2008; 27(2): 255-270.

Neumuth D, Loebe F, Herre H, and Neumuth T, "Modeling surgical processes: a four-level translational approach," Artif Intell Med, 3, pp. 147-61, Netherlands: 2010 Elsevier B.V, 2011.

Neumuth T, Jannin P, Schlomberg J, Meixensberger J, Wiedemann P, and Burgert O, "Analysis of surgical intervention populations using generic surgical process models," Int J Comput Assist Radiol Surg, vol. 6, no. 1, pp. 59-71, January, 2011.

Neumuth T, Straub G, Meixensberger J, Lemke H, Burgert O., "Acquisition of Process Descriptions from Surgical Interventions." Lecture notes in computer science. 2006; 4080:602-11.

Ozkarahan I., "Allocation of Surgeries to Operating Rooms by Goal Programing," Journal of Medical Systems, Vol 24, No 6, 2000.

Padoy N, Blum T, Ahmadi S.-A, Feussner H, Berger M.-O, and N. Navab, "Statistical modeling and recognition of surgical workflow," Medical Image Analysis, vol. 16, no. 3, pp. 632-641, 4//, 2012.

Papaconstantinou H T, Smythe W R, Reznik S I, Sibbitt S, Wehbe-Janek H., "Surgical safety checklist and operating room efficiency: results from a large multi-specialty tertiary care hospital." The American Journal of Surgery 206:853-860, 2013

Payandeh S, Xiaoli Z, Li A, "Application of imaging to the laparoscopic surgery." Paper presented at: Computational Intelligence in Robotics and Automation, 2001. Proceedings 2001 IEEE International Symposium on; 2001, 2001.

Pham D. N., and Klinkert A., "Surgical case scheduling as a generalized job shop scheduling problem,' European Journal of Operational Research, Vol 185, Issue 3, 2008, pp 1011-1025.

Radcliff K E, Rasouli M R, Neusner A, Kepler C K, Albert T J, Rihn J A, Hilibrand A S, Vaccaro A R, "Preoperative delay of more than 1 hour increases the risk of surgical site infection." Spine 38:1318-1323, 2013

Schuster M, Pezzella M, Taube C, Bialas E, Diemer M, Bauer M., "Delays in starting morning operating lists: an analysis of more than 20,000 cases in 22 German hospitals." Deutsches Arteblatt International 110:237-243, 2013

Siciliani L. and Hurst J., "Tackling excessive waiting times for elective surgery: a comparative analysis of policies in 12 OECD countries," Health Policy 2005; 72:201-215.

Sperandio F, Gomes C, Borges J, Brito A C, Almada-Lobo B., "An intelligent decision support system for the operating theater: a case study." IEEE Transactions on Automation Science and Engineering 11:265-273, 2014.

Staub C, Lenz C, Panin G, Knoll A, Bauernschmitt R., "Contour-based surgical instrument tracking supported by kinematic prediction." Paper presented at: Biomedical Robotics and Biomechatronics (BioRob), 2010 3rd IEEE RAS and EMBS International Conference on; 26-29 Sep. 2010, 2010.

Stoll J., Ren H. and Dupont P. E., "Passive Markers for Tracking Surgical Instruments in Real-Time 3-D Ultrasound Imaging," IEEE Transactions on Medical Imaging, Volume 31, Issue 3, pp 563-575, March 2012.

Strum D P, Vargas L G, May J H, Bashein G., "Surgical suite utilization and capacity planning: a minimal cost analysis model." J Med Syst 1997; 21:309-22.

Tatar F, Mollinger J, Bossche A., "Ultrasound system for measuring position and orientation of laparoscopic surgery tools." Paper presented at: Sensors, 2003. Proceedings of IEEE; 22-24 Oct. 2003, 2003.

Tatar F, Mollinger J R, Bastemeijer J, Bossche A. "Time of flight technique used for measuring position and orientation of laparoscopic surgery tools." Paper presented at: Sensors, 2004. Proceedings of IEEE; 24-27 Oct. 2004, 2004.

Voros S, Orvain E, Cinquin P, Long J A., "Automatic detection of instruments in laparoscopic images: a first step towards high level command of robotized endoscopic holders," Paper presented at: Biomedical Robotics and Biomechatronics, 2006. BioRob 2006. The First IEEE/RAS-EMBS International Conference on; 20-22 Feb. 2006, 2006.

Warner C J, Walsh D B, Horvath A J, Walsh T R, Herrick D P, Prentiss S J, Powell R J., "Lean principles optimize on-time vascular surgery operating room starts and decrease resident work hours" Journal of Vascular Surgery, 58:1417-1422, 2013

Xiao Y, Schimpff S, Mackenzie C, Merrell R, Entin E, Voigt R, and Jarrell B, "Video Technology to Advance Safety in the Operating Room and Perioperative Environment," Surgical Innovation, March 2007 14: 52-61.

Yuan, J. S.-C., "A general photogrammetric method for determining object position and orientation," IEEE Transactions on Robotics and Automation, Volume 5, Issue 2, pp 129-142, April 1989.

Polulu Robotics and Electronics force-sensing resistor from Interlink Electronics described at http://www.pololu.com/product/1697 and http://www.pololu.com/product/1645.

Society of American Gastrointestinal and Endoscopic Surgeons, http://www.sages.org/

What is claimed is:

1. A medical procedure monitoring system comprising:
a computer readable medium comprising a plurality of standards for a medical procedure;
a plurality of sensors, wherein the plurality of sensors are located in an operating room and each sensor is configured to:
   detect a parameter of a component used in the medical procedure; and
   provide an output based on the parameter of the component detected; and
a plurality of lights to indicate a proper position of a medical instrument on an instrument table;
a computer processor configured to:
   receive the output from each sensor; and
   compare the output from each sensor to a standard from the plurality of standards for the medical procedure,
   wherein:
      the medical procedure monitoring system is configured to detect the parameter of the component used in the medical procedure and provide the output based on the parameter of the component detected in real-time;
      the plurality of sensors comprises a light sensor to detect when the medical instrument has been removed from the instrument table;
      the output from each sensor automatically provides an n-tuple $(T_1, T_2, \ldots, T_n)$ of positive real numbers for the medical procedure to a mathematical model, where the n-tuple $(T_1, T_2, \ldots, T_n)$ indicates the time at which each specific targeted event occurs and represents a time portrait of the medical procedure; and
      the medical procedure monitoring system is configured to:
         register the time portrait of the medical procedure in a data set;
         compute an average standard time portrait of the medical procedure and a dispersion around the average time portrait; and
         automatically classify the medical procedure as standard or nonstandard based on the time portrait of the medical procedure.

2. The medical procedure monitoring system of claim 1 wherein the time portrait is correlated to a patient outcome after surgery.

3. The medical procedure monitoring system of claim 1 wherein the output provided by each sensor is a binary output.

4. The medical procedure monitoring system of claim 1 wherein the plurality of sensors are sealed from an atmospheric environment in the operating room.

5. The medical procedure monitoring system of claim 1 wherein the plurality of sensors comprises a light brightness sensor.

6. The medical procedure monitoring system of claim 1 wherein the plurality of sensors comprises force-sensing resistor strips.

7. The medical procedure monitoring system of claim 1 wherein the plurality of sensors comprises a force-sensing resistor panel.

8. The medical procedure monitoring system of claim 1 wherein the plurality of sensors comprises a split core current sensor.

9. The medical procedure monitoring system of claim 8 wherein the video camera is configured to detect changes in ambient light intensity.

10. The medical procedure monitoring system of claim 9 wherein the changes in ambient light intensity indicate a differentiation between open and minimally invasive procedures.

11. The medical procedure monitoring system of claim 1 wherein the plurality of sensors comprises a video camera.

12. The medical procedure monitoring system of claim 11 wherein the video camera is directed to a ventilator to detect movement of a bellows.

13. The medical procedure monitoring system of claim 11 wherein the video camera is directed to detect a specific color.

14. The medical procedure monitoring system of claim 1 wherein the plurality of sensors comprise radio frequency identification (RFID) sensors to capture personnel movement in a perioperative space.

\* \* \* \* \*